United States Patent [19]

Pommer et al.

[11] 4,316,384
[45] Feb. 23, 1982

[54] DIGITAL MOISTURE METER AND METHOD FOR DETERMINING PERCENT WEIGHT LOSS

[75] Inventors: Dennis L. Pommer; Paul E. Coleman, both of Minneapolis, Minn.

[73] Assignee: General Mills, Inc., Minneapolis, Minn.

[21] Appl. No.: 72,398

[22] Filed: Sep. 4, 1979

[51] Int. Cl.³ .......................... G01N 5/02; G06G 7/16
[52] U.S. Cl. ................................. 73/76; 235/92 MT; 364/567
[58] Field of Search ..................... 73/76; 364/568, 477, 364/567, 552; 219/10.55 M

[56] References Cited

U.S. PATENT DOCUMENTS

| | | | |
|---|---|---|---|
| 2,047,765 | 7/1936 | Brabender | 73/76 |
| 2,780,095 | 2/1957 | Brabender | 73/76 |
| 2,816,437 | 12/1957 | Hornberger et al. | 73/76 |
| 2,832,215 | 4/1958 | Brabender | 73/76 |
| 3,564,224 | 2/1971 | Chope | 364/469 |
| 3,596,071 | 3/1965 | Doering | 364/469 |
| 3,714,401 | 1/1973 | Yano et al. | 364/567 |
| 3,814,914 | 6/1974 | List et al. | 364/477 |
| 3,839,616 | 10/1974 | Risman | 219/10.55 M X |
| 3,909,598 | 9/1975 | Collins et al. | 73/76 X |
| 3,916,670 | 11/1975 | Davis et al. | 73/76 |
| 4,153,122 | 5/1979 | Engels et al. | 364/567 X |
| 4,165,633 | 8/1979 | Raisanen | 73/76 |
| 4,168,623 | 9/1979 | Thomas, Jr. | 73/76 |

*Primary Examiner*—Daniel M. Yasich
*Attorney, Agent, or Firm*—Gene O. Enockson; L. MeRoy Lillehaugen; Stuart R. Peterson

[57] ABSTRACT

The digital moisture meter includes means for taring an empty sample pan placed on the balance platen. After the balance has been tared, a small sample is placed in the sample pan and a heat lamp energized. At this same time, the initial weight of the sample is stored in memory and after twenty seconds a first calculation is made to determine the percent weight loss, the value of which is also stored in memory. Subsequent percent weight loss values are calculated and if the latest percent weight loss is greater than the one that has been stored in memory, the stored one is then replaced with the latest value. However, if the latest percent weight loss value is less or equal to the stored value, the stored value is retained in memory for comparison with the next percent weight loss value that is calculated. When the percent weight loss value remains constant for a predetermined number of checks, the stored percent weight loss that has remained constant is then considered to be the correct value and is both visually displayed and printed. Provision is made for energizing the heat lamp at its full intensity for a preselected period of time and then reducing the intensity of the heat lamp so that the sample dries more slowly and thus does not burn or lose volatile non-water ingredients.

4 Claims, 3 Drawing Figures

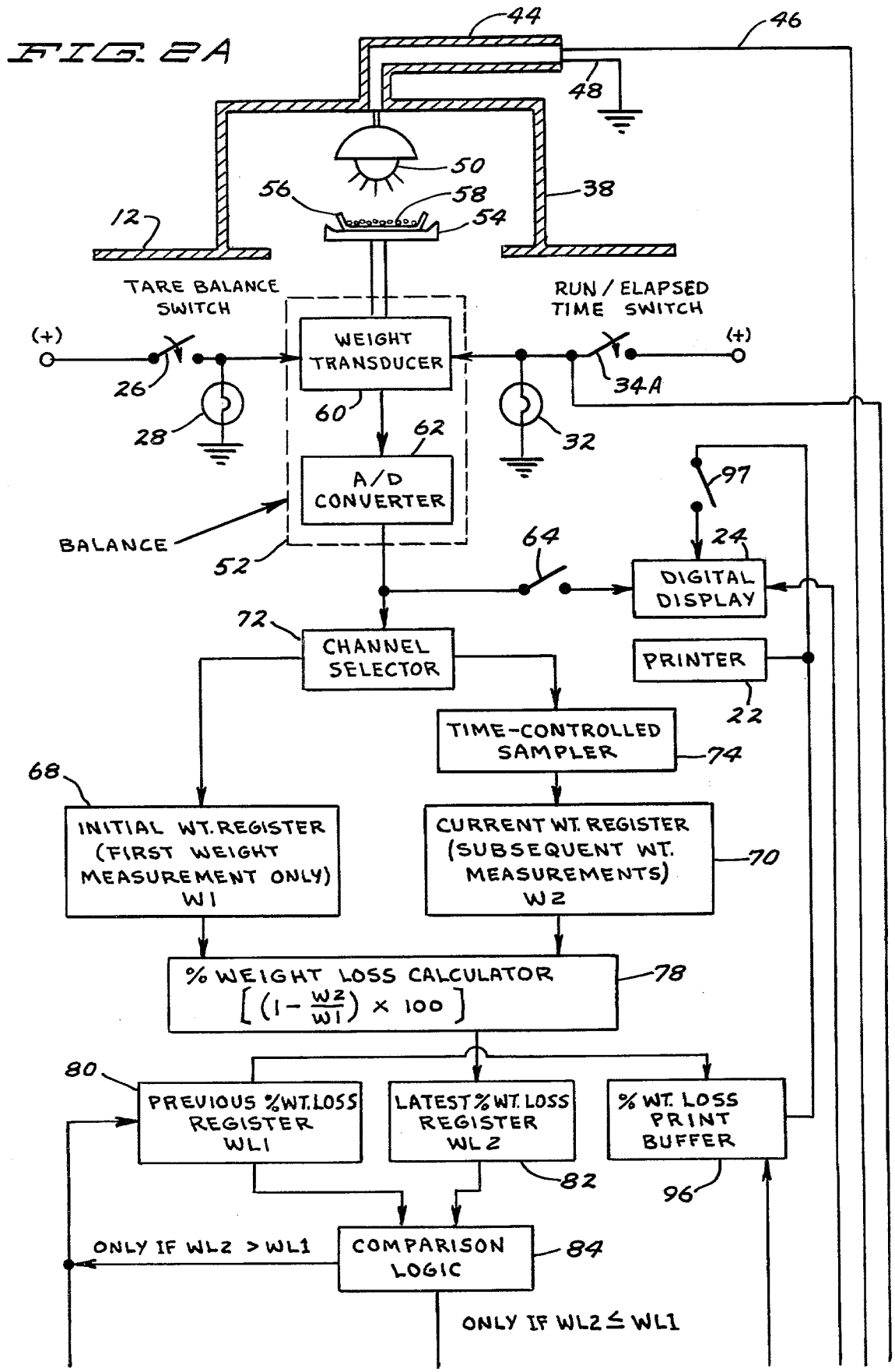

DIGITAL MOISTURE METER AND METHOD FOR DETERMINING PERCENT WEIGHT LOSS

BACKGROUND OF THE INVENTION

1. Field of the Invention

This invention relates generally to a digital moisture meter and to a method for determining the percent weight loss in a relatively small sample, the moisture of which is to be determined, and pertains more particularly to a meter and method that will find especial utility in ascertaining the percent weight loss at various stages in the manufacture of a cereal product or the like.

2. Description of the Prior Art

In the past, the determination of moisture in a given product or sample has been accomplished in several different ways. One of the most accurate ones with which we are familiar is the analytical method of drying within a vacuum-type oven. In such a situation, a sample is physically weighed prior to placing it within the vacuum oven and then waiting a sufficient length of time for the sample to be heated in the low pressure or sub-atmospheric environment. At a later time the sample is taken out and the sample then weighed. An assumption is made that only moisture is driven off. The percent weight loss is then calculated from the original weight of the sample and the ultimate or final weight after the moisture has been driven off. Such a procedure is prone to human error and it is also quite time consuming.

Another method for determining the amount of moisture in a given product involves the heating of a sample within an oil bath. First, the sample is weighed prior to placing it in the bath and then after it has been put into the oil, the resulting mixture is again weighed. After the mixture has been heated, that is boiled, for a sufficient time to get rid of the moisture, the oil bath with the sample therein is again weighed. From this data, the percent moisture is computed. Here again, the process is entirely too slow for moisture investigations during a high speed commercial or industrial process, such as the cooking of cereal products.

SUMMARY OF THE INVENTION

Accordingly, an important object of our invention is to determine the percent weight loss at various stages of an industrial process so that corrective adjustments can be made within a reasonable length of time. In this regard, an aim of the invention is to permit the taking of only a small sample of the product so that it can be dried more rapidly and thereby reduce the amount of time involved as far as determining the percent moisture of the product.

Another object of the invention is to provide a digital moisture meter that will be quite accurate. Also, it is within the contemplation of our invention to take a sample that may vary in weight, for our method enables the operator to use virtually any amount of product as the sample to be checked. Although the precise amount of the product that is selected is relatively unimportant, it should be appreciated that when large amounts are used, then the drying period is increased accordingly. Since our invention permits only a small sample to be utilized in the investigative procedure, as indicated above, the entire checking time is quite short.

A further object of our invention is to provide a digital moisture meter and method which is not dependent on the capabilities of the person using the meter. Stated somewhat differently, an aim of the invention is to provide a method of determining the percent weight loss that is extremely simple and which does not require any special training as far as the person operating the digital moisture meter is concerned.

Yet another object of our invention is to provide a digital moisture meter that requires very little energy as far as its operation is concerned. In this regard, it is within the purview of the invention to employ a heat lamp that has a wattage on the order of only 125 watts. Not only does a heat lamp of this relatively low wattage rating enable a more accurate moisture check to be made, but our invention provides for decreasing the intensity of the heat lamp towards the end of the drying procedure so that the sample will not be burned and will also not lose weight by reason of other volatile or non-water ingredients being driven off which would adversely affect the precision of the moisture determination.

Still further, an object is to provide a digital moisture meter that requires no initial calibration, it only being necessary to tare the balance with no sample placed in the pan on the platen so that whatever sample is then placed in the sample pan will be initially weighed, and its reduced weight by virtue of losing moisture will be repeatedly checked until virtually all of the moisture has been removed.

Another object of our invention is to provide a digital moisture meter in which no venting is needed, this being so by reason of the relatively small amount of sample that can be used.

Briefly, our invention envisages the initial taring of the balance by placing an empty sample pan on the balance platen. A check is made of a seven segment digital display to determine when the balance has reached its true zero condition. It is then that a small sample of the product to be checked is placed in the pan and the initial weight of the product, after being converted to a digital value, is stored in a memory for future use. At the same time, a heat lamp is turned on and the drying process is initiated. After twenty seconds, this being a sufficient time so that the sample can begin losing moisture, a second digital weight value is determined, and by means of a calculator the latest weight is compared with the initial weight so as to provide a percent weight loss value. The percent weight loss value that is thus determined is also stored and if the next percent weight loss value is greater than that which has just been stored, then the new or later value is stored, replacing the preceding stored percent weight loss value. On the other hand, if the new or latest percent weight loss value is less than or equal to the previous or preceding stored value, the previous or preceding value is retained in memory.

A compare counter continually compares the latest percent weight loss value to the previous percent weight loss value and after there is no change for a preselected number of checks, then the sample is deemed to be fully dried and the resulting percent weight loss value a true value. At this stage, a printout of the true percent weight loss value is made and also the value is displayed digitally so that the operator will recognize that the procedure has been completed. The operator also knows that the procedure has been completed because the heat lamp is turned off.

Provision is made for reducing the heat lamp toward the end of the drying cycle so that the sample will not be burned and also will not lose any weight attributable to its non-hydrous composition. Until the stabilized or consistent weight loss values are achieved, the steps are automatically repeated at frequent intervals so that the final percent weight loss value is made known just as soon as its stabilized condition is reached.

DESCRIPTION OF THE PREFERRED EMBODIMENT

Figure 1:
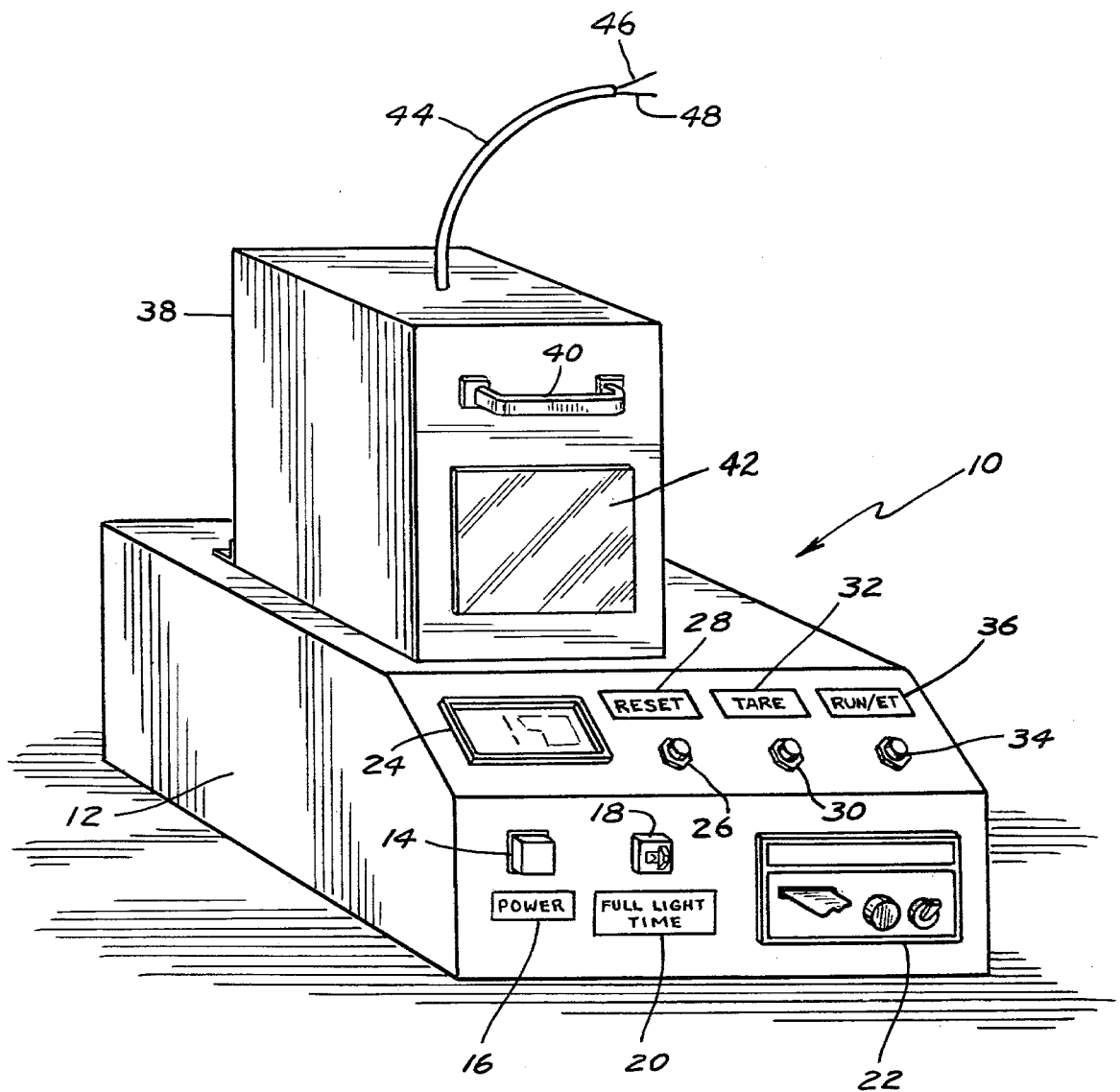
FIG. 1 is a perspective view of the digital moisture meter exemplifying our invention, and FIGS. 2A and 2B when placed one above the other constitute a block diagram exemplifying our moisture meter.

Referring first to FIG. 1, the digital moisture meter in accordance with our invention has been designated generally by the reference numeral 10. The meter 10 includes a console 12 within which is contained the various components for carrying out our invention. It is to be observed that the console has a power switch 14 and indicating lamp 16, a full light selector switch 18 and full light time indicator 20, and a print-out device 22.

Still further, the moisture meter 10 includes a digital display 24. Just to the right of the digital display 24 is a reset pushbutton 26. Also, there is a tare switch 30 with an indicating lamp 32 thereabove. Still further, a run-/elapsed time switch 34 has an indicating lamp 36 associated therewith.

Owing to the fact that only small samples are to be checked with the moisture meter 10, it is important that a hood 38 be employed to avoid inaccurate determinations because of air currents. The hood 38 has a handle 40 so that it can be readily lifted from the console 12. The hood 38 also has a viewing window 42. Extending through the top of the hood 38 is a power cord 44 containing a pair of conductors 46, 48 therein.

Although not shown in FIG. 1, it can be perceived from FIG. 2A that the power cord 44 leads to a heat lamp 50. It can be mentioned at this stage of the description that the heat lamp 50 need not be a large one, for in actual practice it has been found that a 125 watt infrared lamp is sufficient.

Although concealed by the hood 38 in FIG. 1, from FIG. 2A it will be seen that a balance denoted generally by the reference numeral 52 appears. This balance 52 is mounted within the console 12 so that its platen 54 projects above the upper surface of the console 12. The platen 54 supports a removable sample pan labeled 56. Although it will be better understood as the description progresses, the pan 56 is used to contain a small sample 58 of the product the moisture of which is to be determined. More specifically, it can be pointed out at this time that approximately 7 to 15 grams of the product to be investigated as to its moisture content can serve as an adequate sample 58.

Inasmuch as the balance 52 can be of conventional construction, all that need be explained at this time is that a weight transducer 60 is included in the balance 52 which provides an analog signal indicative of whatever weight is placed on the balance platen 54. The analog signal provided by the transducer 60 is converted to a digital signal by means of an analog-to-digital converter 62, also part of the balance 52. The output from the A/D converter 62 is delivered to the digital display 24, there being a switch 64 depicted in the illustrated situation by means of which the converter 62 can be connected or disconnected with respect to the display 24. Switch 64 may be a simple electromechanical switch or may be a complex electronic switching network.

It will be helpful at this point, it is believed, to explain that when the pan 56 is empty, the balance 52 is tared by first depressing reset pushbutton 26, then closing the switch 30. The actual means for achieving the taring is conventional and need not be described in any detail. It will be recognized, though, that when the tare signal has been reduced to zero, then the A/D converter 62 will forward a zero digital signal to the display 24 via the switch 64. In actual practice, the display 24 is a seven segment display so that a very precise zero reading in digital form will appear on the display 24 when the balance 52 is truly tared.

Figure 2B:
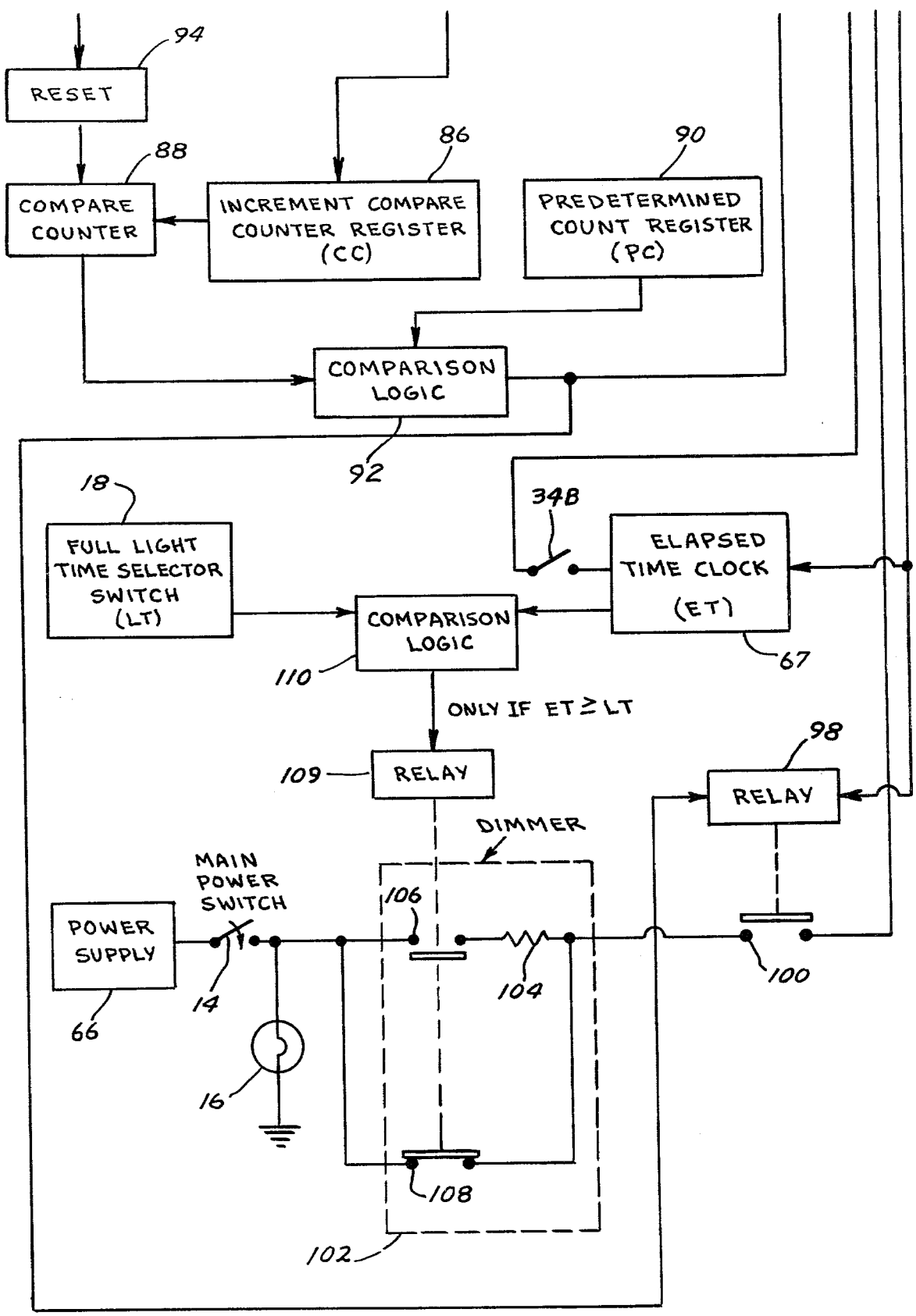

Inasmuch as the block diagram pictured in FIGS. 2A and 2B is a simplification of the circuitry embodied in our actual digital moisture meter 10, certain details and refinements have been omitted for simplicity reasons. In this regard, it can be pointed out at this stage that if a logical zero is not realized within twenty attempts, the printer 22 will print a tape stating that the meter balance 52 has not been tared, and the operator is in this way apprised of the malfunctioning of the meter 10. He can then conduct an investigation to ascertain what is wrong.

The run/elapsed time switch 34 is comprised of two switch sections 34A and 34B which are latched together to provide a predetermined sequence of operation. When the first time switch 34 is activated switch section 34A closes to energize an elapsed time (ET) clock 67 and a relay 98. Any subsequent activation of switch 34 will cause section 34B to momentarily close, thereby transferring the elapsed time clock 67 value to digital display 24. When reset switch 26 is activated switch 34 becomes reset to permit a repeat of its actuation sequence.

Assuming that the taring action described above has been properly completed, a small sample 58 is placed on pan 56, and then switch 34 can be closed which energizes relay 98 which connects the heat lamp 50 to a power supply denoted generally by the reference numeral 66.

The first closing of the run/elapsed time switch 34 starts the clock 67. At any subsequent closure of the switch 34 the time that has elapsed during the drying procedure will be visually displayed on the display 24 to the operator.

The output from the A/D converter 62 is stored in memory, either in a first register 68 or a second register 70. To accomplish this, a channel selector switch 72 has been included in the block diagram illustrating our invention. The selector 72 directs to the first register 68 a digital signal having a value representative of whatever weight of sample 58 is placed in the sample pan 56. Consequently, as soon as the sample 58, which is on the order of from 7 to 15 grams, is placed in the pan 56, the transducer 60 forwards an analog signal to the A/D converter 62 which sends a digital signal to the register 68 which is indicative of the initial weight of the sample 58 that is to be dried. Thus, whatever weight is initially found to be on the pan 56 has its value digitally stored in the register 68.

It should be understood that the amount of sample 58 placed in the pan 56 is not critical in any sense of the word. The criteria really centers around having enough weight so that an accurate determination of its moisture content can be made, yet not be so massive that the drying procedure is prolonged unduly. Consequently, from experience, it has been ascertained that a sample on the order of from 7 to 15 grams constitutes a practical weight range.

Because it takes some time before moisture is removed from the sample 58 in the pan 56, there is no need to take a later weight reading until after a sufficient time has elapsed to achieve a discernible weight loss. A suitable such time has been found to be 20 seconds. Therefore, the next or second weight reading is taken after the lamp 50 has been energized for 20 seconds, and, of course, 20 seconds after the initial weight value has been stored in the register 68. The second weight reading, however, is stored in the second register 70, the channel selector 72 switching from the register 68 to the register 70 so that signals arriving from the A/D converter 62 are fed to the register 70 instead of the register 68. To introduce the predetermined delay, which has been mentioned as being 20 seconds, a time-controlled sampler 74 is employed. As its name implies, the sampler simply samples the digital data from the converter 62 that is made available via the channel selector 72, doing so at predetermined intervals. While the first interval is 20 seconds, subsequent intervals can be the same, greater or less than this figure; intervals of ten seconds have been employed.

For the sake of facile explanation, the initial weight value stored in the register 68 will be indicated by the letter W1, whereas the latest weight value stored in the register 70 will be denoted by the letter W2.

At this time, attention is directed to a digital calculator 78 which computes the percent total weight loss as follows: $[(1-W2/W1) \times 100] = \%$ total weight loss The percent total weight loss, which steadily increases as the drying progresses, will be represented by WL. It will vary during the heating period, that is, during the time the heat lamp 50 is energized. Also, it will be appreciated that the register 70 accepts whatever latest weight reading W2 that is fed into it. Each time that the weight of the sample 58 contained in the pan 56 is measured and the value thereof forwarded via the selector 72 and sampler 74 to the register 70, the digital weight value in the register 70 will be changed so that the designation W2 always represents the latest weight value irrespective of when it has been fed into the register 70. However, as far as the initial weight W1 is concerned, it remains in the register 68 throughout the entire cycle.

Whereas the registers 68, 70 constitute a weight memory or storage, a second or percent weight loss memory is provided, being comprised of a first register 80 and a second register 82. The second register 82 is connected to the calculator 78 so that whatever percent weight loss value is computed by the calculator 78 will be forwarded to the register 82 for storage.

At this point, it will be of benefit to state that the so-called previous percent weight loss value in the register 80 will be denoted by the letters WL1 and the latest percent weight loss value stored in the register 82 by the letters WL2. It will be appreciated that the value of WL2 is constantly changed as the sample 58 continues to lose moisture during the weighing cycle.

It is the function of a comparison logic circuit 84 to check the data stored in the registers 80, 82 to ascertain whether WL2 is greater than WL1 or if WL2 is less than or equal to WL1.

If the former condition immediately above exists, then the latest percent weight loss, that is WL2, is transferred to the register 80. By doing this, the latest percent weight loss, whatever it is, replaces or writes over the percent weight loss value stored in the register 80 and becomes the WL1 value that is used in subsequent comparisons by the comparison logic 84. Reset 94 is also activated to reset compare counter 88 to zero.

On the other hand, if the latter situation prevails, that is WL2 is less or equal to WL1, the value of percent weight loss WL1 already stored in the register 80 is left there, that is, not changed or replaced. However, the comparison logic 84 generates a signal to an increment compare counter register 86 which increments a compare counter 88 by "one".

Assurances are incorporated into the meter 10 for the purpose of making certain that the sample 58 in the pan 56 has become fully dried. Therefore, if the first check shows that WL2 is either greater or equal to WL1, this condition should be repeatedly checked for a given number of times before it is accepted as the true and final percent weight loss value. Accordingly, a predetermined count register 90 is connected to an additional comparison logic circuit 92 which logic 92 compares whatever predetermined count that has been selected and stored in the register 90 with the count actually reached by the compare counter 88. In practice the predetermined count found sufficiently reliable is "four". Thus, when the compare counter 88 has established that WL2 is less than or equal to WL1 for the selected predetermined number of times, actually "four" in practice as mentioned above, it, in effect, terminates the drying and weighing process.

Backtracking for a moment, it will be recalled that if WL2 is greater than WL1, then the new WL2 is stored in the register 80, replacing the previously stored WL2 value stored in this particular register. Should WL2 again become greater after WL2 has become less than or equal to WL1 (for any reason whatsoever), then the compare counter 88 should be reset to zero from its "one", "two" or "three" count, for, as stated above, the count must reach "four" to denote a reliable and stabilized weight loss condition of the sample 58. Therefore, whenever the comparison logic 84 outputs a "WL2 greater than WL1" signal to the register 80, a signal is simultaneously forwarded from the comparison logic 84 to a reset circuit 94 that returns the compare counter 88 to zero. In other words, the counter 88 must start counting all over again, and must reach the selected count of "four" before the weighing operation or cycle is regarded as completed. When a count of "four" is reached by the counter 88, then the comparison logic 92 outputs a digital signal to a print buffer 96 which has also been storing the WL1 digital signals, and hence contains therein the latest WL1 value which is now the final WL2 value and hence is the percent total weight loss value that is truly indicative of the precise moisture loss from the sample 58.

The print buffer 96, by reason of the control signal forwarded from the logic circuit 92, causes the printer 22 to print out a tape with the final total percent weight loss figure thereon. This same figure is simultaneously made available to the digital display 24 via switch 97 which may be activated once during each sample period. Switch 97 can be activated by sampler 74 through an electronic circuit (not shown).

Since the measuring procedure has been consummated when the predetermined counter 88 reads a "four" count, the relay 98 is deenergized by the comparison logic 92 output signal, the relay 98 having normally open contacts 100 in circuit with a dimmer 102. While the dimmer 102 can be a solid state device, for the sake of picturing what happens, it is assumed to have a fixed resistance 104 (or the resistance 104 can be a rheostat) in series with normally open contacts 106 and in parallel with normally closed contacts 108, these contacts 106, 108 belonging to a relay 109. The relay 109 is energized by means of a comparison logic circuit 110 connected between the previously mentioned full light time selector switch 18 and the elapsed time clock 67. Whereas the logic 110 causes the intensity of the heat lamp 50 to be reduced, the logic 92 interrupts the power to the lamp 50 when the drying has been completed, doing so by means of a signal to the relay 98. Thus, when the entire weighing and drying procedure has been concluded, the heat lamp 50 is automatically deenergized.

Actually, the selector switch 18 is of the thumbwheel type which enables the operator to manually select the length of time that the heat lamp 50 remains fully energized, that is at its highest intensity. By selectively setting the time for the lamp 50 to be fully energized, the first portion of the drying procedure can be effected at an accelerated rate, but as the sample 58 in the pan 56 becomes dryer and dryer, it follows that the sample 58 should not be burned or heated to such an extent that non-water moisture or volatile substance is driven off. In other words, the heat lamp 50 is energized through the relay 98 and relay 109. When the resistance 104 in the dimmer 102 is bypassed by the normally closed contacts 108, then the full 120 volts AC are impressed on the lamp 50. However, when relay 109 becomes energized the contacts 108 are opened and contacts 106 are closed, which happens when the time selected by the selector switch 18 has completely elapsed. The power supplied to the heat lamp 50 then will be reduced to lower its light output. 60% of the initial or original power has been found satisfactory for most products to be analyzed, particularly when of a cereal character.

It should be understood that when the percent weight loss WL2 has not stabilized, the compare counter 88 then does not equal "four" as determined by the predetermined register 90. Hence, the steps needed to continue calculating new percent weight loss values WL2 will continue until the total weight loss has become constant. This is done at intervals in practice of approximately delays of ten seconds until the finalized percent weight loss has been reached.

In summation, it will be seen that our digital moisture meter 10 works on a weight loss principle, requiring no calibration. Only small samples need be used, ranging as a practical matter from 7 to 15 grams. The accuracy in actual practice is quite high, being on the order of ±0.2% moisture. The whole procedure for a sample containing 12% moisture takes only from 6 to 8 minutes, the time being correspondingly shorter for lower moisture samples.

Whenever the elapsed time is to be observed, it can be determined very readily and the final moisture results are not only visually displayed but also printed on a readout tape. The operator requires little or no training and has no influence on the results realized when practicing our invention. Still further, the accuracy of the entire procedure is not at all affected by the size of heat lamp 50 and the heat lamp 50 can be replaced as circumstances dictate without making any compensating adjustments for the new lamp.

We claim:

1. A digital moisture meter comprising a balance including a platen for receiving a sample thereon and means for providing a digital signal having a value in accordance with the initial weight of the sample on said platen and also successive later digital signals having digital values representative of later reduced weights of said sample, means for heating said sample to remove moisture therefrom, means for reducing the intensity of said heating means after a predetermined time interval, first means for storing said digital signal having a value representative of the initial weight of said sample, second means for storing said later digital signals having a value representative of a subsequent reduced weight, each of said later digital signals being successively stored in said second storing means, calculating means responsive to the value of said digital signal stored in said first storing means and the value of said digital signal stored in said second storing means at a given time for providing a digital signal having a value representative of the percent weight loss for each successively stored later digital signal, third means for storing one of said digital signals having a value representative of percent weight loss, fourth means for storing a later digital signal having a value representative of a later percent weight loss, means for comparing the value of said one digital signal stored in said third storing means with the value of the digital signal stored in said fourth storing means and for substituting the digital signal stored in said fourth storing means for the one stored in said third storing means if greater in value than the one already stored in said third storing means, means for displaying the value of said digital signal stored in said third storing means if the value stored in the fourth storing means is less than or equal to the signal stored in said third storing means, and means for disconnecting said heating means only after a predetermined number of successive digital signals stored in said fourth means have a value less than or equal to the digital signal stored in said third storing means and have thus denoted a stabilized weight loss condition.

2. A digital moisture meter comprising balance means including a platen for receiving a sample therein and means for producing digital signals having values in accordance with the weight of the sample on said platen, means above said platen for heating said sample, first and second registers, means for forwarding a first digital signal having a value representative of the initial weight of said sample to said first register for storage therein and for subsequently forwarding successive digital signals having values representative of later weights of said sample to said register for storage therein, calculating means for receiving the digital signals stored in said first and second registers to provide successive digital signals each of which has a value representative of the percent weight loss of said sample for each of said successive digital signals, third and fourth registers, said fourth register storing said digital signals having values representative of the percent weight loss, and comparing means connected to said third and fourth registers for transferring the latest digital signal stored in said fourth register to said third register when the value of the latest digital signal stored in said fourth register is greater than the digital signal stored in said third register and in which the digital signal stored in said third register is retained in said third register when said digital signal in said fourth register is less than or equal to the digital signal stored in said third register, means for counting the number of times the latest digital signal stored in said fourth register is less than or equal to the digital signal stored in said third register, and means responsive to said last-mentioned means for disabling said heating means after said last-mentioned means has reached a predetermined count and has thus denoted a stabilized weight loss condition.

3. A method of determining the percent moisture loss in a relatively small sample comprising the steps of obtaining a first digital signal having a value representative of the initial weight of said sample, storing said first digital signal, subjecting said sample to a source of heat, obtaining a second digital signal having a value representative of the weight of said sample at a later time, storing said second digital signal, calculating from said first and second digital signals a third digital signal having a value representative of the percent weight loss, storing said third digital signal, obtaining a fourth digital signal having a value representative of the weight of said sample at a still later time, storing said fourth digital signal, calculating from said first and fourth digital signals a fifth digital signal having a value representative of the percent weight loss occurring at said still later time, comparing said third and fifth digital signals to ascertain whether the fifth digital signal has a value greater than that of said third digital signal, or less than or equal to the value of said third digital signal, continuing to subject said sample to said heat source if the value of said fifth digital signal is greater than the value of said third digital signal, and removing said heat source when the value of said fifth digital signal is equal to a predetermined value.

4. A method in accordance with claim 3 including the steps of obtaining additional third and fifth digital signals and determining when a predetermined number of fifth digital signals are less than or equal to a third digital signal, said predetermined number of fifth digital signals when less than or equal to a third digital signal denoting a stabilized weight loss condition.

* * * * *